United States Patent [19]

Urahama et al.

[11] 4,279,213
[45] Jul. 21, 1981

[54] RESIN MOLDED PRODUCTIONS DESIGNED TO DISPLAY EXTINCTION OF ACTIVITY

[75] Inventors: Yoshiaki Urahama; Tetuo Numoto, both of Ibaraki, Japan

[73] Assignee: Nitto Electric Industrial Co., Ltd., Ibaraki, Japan

[21] Appl. No.: 132,344

[22] Filed: Mar. 20, 1980

[30] Foreign Application Priority Data

Mar. 20, 1979 [JP] Japan ............................ 54/35973[U]

[51] Int. Cl.³ ......................................... G01N 21/17
[52] U.S. Cl. ..................................... 116/200; 356/256; 116/201; 422/57; 424/7; 428/907; 428/913
[58] Field of Search ............... 116/200, 201, 206, 207, 116/208, 216, 219, 278, DIG. 14; 23/230 R; 422/56, 57; 427/145; 428/201, 199, 907, 913; 43/131, 132 R; 356/256; 424/7, 78

[56] References Cited

U.S. PATENT DOCUMENTS 4,062,649 12/1977 Kuderna et al. .................. 23/230 R

*Primary Examiner*—Arnold Turk
*Attorney, Agent, or Firm*—Sughrue, Rothwell, Mion, Zinn and Macpeak

[57] ABSTRACT

In a resin molded controlled-release product which comprises a volatile or elutable active agent dispersed in a substantially transparent and inert resin molded material, the improvement which comprises a colored material located inside or on the back surface of the molded product which is not visible through the product at the initial concentrations of the active agent, but is visible through the resin product at concentrations of the active agent at which the activity of the product is substantially extinct.

6 Claims, 5 Drawing Figures

1

RESIN MOLDED PRODUCTIONS DESIGNED TO DISPLAY EXTINCTION OF ACTIVITY

BACKGROUND OF THE INVENTION

1. Field of the Invention:

The present invention relates to resin molded products which are designed to display extinction of activity.

2. Description of the Prior Art:

There have been known in the art so-called controlled-release products which are adopted to slowly release active agents, (e.g., fungicides, pesticides, etc.) incorporated into inert resin molded products. With such controlled-release products, as might be expected from their retention of activity for a prolonged period, eventually the time during which the active agents are released effectively lapses and the rate of release of the active agents becomes too low to recognize the extinction of activity. Further, since the rate of release of active agents from controlled-release products may vary depending on temperature, humidity and other conditions, their service lives are not always constant and the effective period indicated on the product label can only supply a very rough estimate. Accordingly, it is often the case with such products that exhausted materials are falsely thought to be active or materials still retaining satisfactory activity are thought useless and discarded.

U.S. Pat. No. 4,062,649 discloses a method for indicating depletion of controlled-release pesticide formulations which relies upon a color change in an acid-base indicator. The method, however, requires the incorporation of no less than two additional reagents in the pesticide formulation and, as such, it is not cost effective. In the case of oxygen absorbents, a product is known (Ageless by Mitsubishi Gas Chemical Co.) which is designed to display the exhaustion of activity by incorporating a reagent which will react with oxygen and change color when the active agent has been depleted and oxygen has resumed its presence in the atmosphere. However, the art holds little information on controlled-release products in which the resin molded product itself is designed to display extinction.

SUMMARY OF THE INVENTION

The present invention is directed to providing resin molded controlled-release products which are designed to visually indicate the extinction of activity when the release of volatile or elutable active agents has substantially ceased.

Accordingly, the present invention is an improvement in a resin molded controlled-release product which comprises a volatile or elutable active agent dispersed in a substantially transparent and inert resin molded material. The improvement comprises a colored material located inside or on the back surface of the molded product which is not visible through the product at the initial concentrations of the active agent, but is visible through the resin product at concentrations of the active agent at which the activity of the product is substantially extinct.

BRIEF DESCRIPTION OF THE DRAWINGS

The present invention will be described in reference to the drawings in which:

FIGS. 3 and 4 are perspective views of resin molded products in accordance with the present invention, showing how they display the extinction of activity.

DETAILED DESCRIPTION OF THE INVENTION

Figure 1:
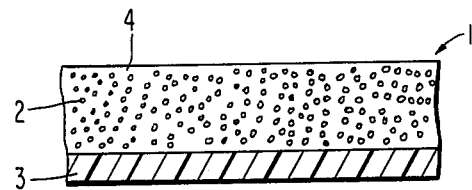
FIG. 1 is a vertical cross-sectional view of a resin molded product in accordance with the present invention.

Referring to FIG. 1, an active agent 2 is dispersed in a resin molded product 1 in the form of a sheet or film to the back surface of which is applied a layer of paint as the layer of a colored material 3. Although the resin constituting the resin molded product 4 is transparent and inert typically, the resin molded product becomes opaque when the active agent is dispersed above its saturation solubility or as minute particles or powder. Therefore, the paint layer on the back surface of the resin molded product is not visible from the front surface. Thus, as long as the active agent is present in the resin molded product above its saturation concentration, it evaporates or is eluted from the resin molded product at a nearly constant and slow rate.

Figure 2:
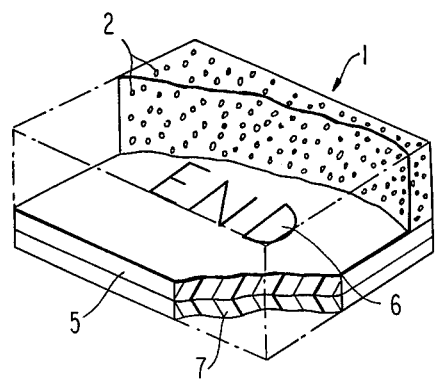
Figure 4:
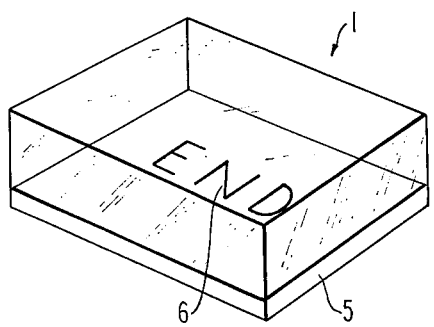

The colored material may be applied by coating the back surface of the resin molded product 1 with a paint as described above or alternatively a colored film 5 may be bonded to the back surface as shown in FIG. 2. Further, it is also possible to place a message such as "FINISH", "END" etc. on the back surface or on the above colored film and such that it is visible from the front surface and conveys the message when the resin molded product becomes transparent, as explained below.

Figure 3:
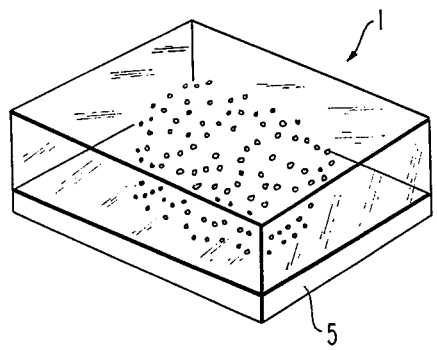
FIG. 3 is a partial perspective view of another resin molded product in accordance with the present invention.

As the release of the active agent proceeds, the concentration of the active agent approaches the saturation concentration at the periphery of the resin molded product first and as shown in FIG. 3. As the periphery becomes transparent, the colored film 5 on the back surface starts to become visible from the front surface of the resin molded product, but the central portions remain opaque. With further release of the active agent, the concentration in the central area gradually approaches the saturation concentration and the resin molded product becomes transparent throughout, thus making the colored film 5 visible from the surface. If the colored film 5 contains a message 6, a change in the color of the resin molded product is observed and at the same time the message advising extinction of activity can be read from the front surface. The foregoing illustration is based on the observation that after the active agent nearly reaches its saturation concentration throughout the whole resin molded product, the release of the active agent suddenly drops; thus the time when the whole resin molded product becomes transparent can be used as the time of extinction of activity.

Next, as shown in FIG. 2, in the present invention, an adhesive layer 7 may also be applied to the under surface of the colored film 5, more generally on the under surface of the colored material layer. The adhesive layer may be formed by coating the colored material layer with an adhesive or bonding a double-colored adhesive tape onto the colored material layer. This facilitates the use of a sheet or film-like resin molded product by enabling it to be adhered to an appropriate location.

Figure 5:
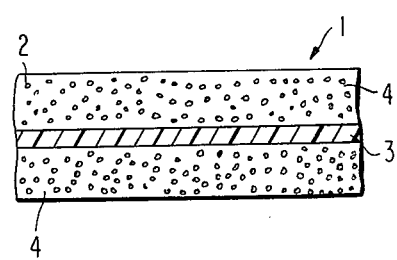
FIG. 5 is a vertical cross-sectional view of an alternative resin molded product in accordance with the present invention.

In the present invention, as shown in FIG. 5, sheets or films incorporating the active agent 2 may be laminated and the layer of the colored material 3 may be applied to the back surface of the undermost layer sheet or film, or inserted between the intermediate sheets or films.

Further in the present invention, the shape of the resin molded product is not limited to the sheet and film exemplified above and, although not specifically illustrated in the drawing, it may also be spherical or polyhedral and the colored material may be located inside.

In the present invention, the active agent is a material which evaporates from the resin molded product into the atmosphere or other gaseous environment or which is eluted into a liquid such as water, organic solvent etc. or into the soil. Preferred examples of such active agents include but are not limited to agricultural chemicals, e.g. fungicides such as o-phenylphenol, p-chloro-m-xylenol, "Amical 48" (by Abbot Laboratories, U.S.A.), α-bromocinnamaldehyde, sorbic acid etc., herbicides such as 2,4-D etc., plant growth regulators such as indoleacetic acid etc., corrosion inhibitors such as benzotriazole, dicyclohexylammonium caprylate, cyclohexylammonium molybdate, cyclohexylamine carbonate etc., antioxidants such as 2,6-di-tert-butyl-4-methylphenol etc., and UV absorbers such as p-tert-butylphenylsalicylate etc.

Examples of the resins in which these active agents are incorporated include but are not limited to thermoplastic resins such as polyethylene, ethylene/vinyl acetate copolymer, polypropylene, polyvinyl chloride, acrylic resins, polystyrene, silicone resins, fluorine-contained resins, polyesters, cellulose resins, urethane resins, etc. and thermosetting resins such as epoxy resins, urethane resins, polyester resins, etc.

The particular resin is chosen depending on the solubility of the active agent to be employed, the shape of the molded product, the application conditions etc. For example, in the case of p-chloro-m-xylenol, when it is present in amounts of about 5% by weight or more in polyethylene the resin molded product is blushed, while in ethylene/vinyl acetate copolymers containing 19% by weight and 40% by weight of vinyl acetate, respectively, the resin molded products are blushed when p-chloro-m-xylenol is present in amounts of about 20% by weight or more and about 30% by weight or more, respectively.

The resin molded products in accordance with the present invention may be produced by blending an active agent in an appropriate amount exceedng its saturation concentration and a resin with heating, if necessary, and molding the blend into a sheet, film, sphere or other desired shape.

The present invention is more particularly described in the following examples which are illustrative only. All parts are by weight.

EXAMPLE 1

100 parts of polyvinyl chloride (135 J produced by Japanese Zeon Co., Ltd.), 50 parts of DOP (di-(2-ethylhexyl)phthalate) and 100 parts of fungicide, p-chloro-m-xylenol, were blended with heating, molded into a sheet of 1 mm in thickness at 150° C. and allowed to cool to room temperature. This white opaque sheet was painted green on the back surface and allowed to stand in a constant temperature chamber at 30° C. On the tenth day, the green color on the back surface became visible at the periphery of the sheet and in 54 days the entire sheet displayed the green.

EXAMPLE 2

100 parts of the same polyvinyl chloride as in Example 1, 50 parts of DOP and 50 parts of volatile corrosion inhibitor, benzotriazole were blended with heating and molded into a sheet of 1 mm in thickness at 140° C. This white opaque sheet was painted green on the back surface and allowed to stand in a constant temperature chamber at 30° C. After six months, the whole sheet became transparent and the green colored surface could be seen through the sheet from the front surface.

EXAMPLE 3

100 parts of ethylene/vinyl acetate copolymer (P-1907, vinyl acetate content of 19% by weight, produced by Mitsui Polychemical Co., Ltd.) and 25 parts of powder fungicide, "Amical 48" (produced by Abbott laboratories, U.S.A.) were mill-mixed and molded into a sheet of 0.5 mm in thickness. Two yellow opaque sheets thus obtained were bonded to both sides of a back polyethylene film thereby forming a three-layered resin molded product. This molded product was immersed in water at normal temperature. One year later, the whole sheet had come to look black.

EXAMPLE 4

100 parts of ethylene/vinyl acetate copolymer "P-1907" and 70 parts of p-chloro-m-xylenol were heated to 100° C., mill-mixed and molded into a sheet of 1 mm in thickness. The whole body of the sheet thus obtained was white and opaque. A white sheet of paper including the message "END" in black was bonded at the center of the black surface of the sheet, which was then stored in a constant temperature chamber at 30° C. One month later, the periphery of the sheet became transparent and the entire body of the sheet was visible in six months, and thus the message could be clearly read from the front surface.

EXAMPLE 5

30 parts of fine powder α-bromocinnamaldehyde which had been passed through a wire sieve of 100 mesh and 25 parts of DOP were blended and added with stirring to 100 parts of urethane prepolymer having a molecular weight of approximately 1000 (Soflannate 2013 produced by Nihon Soflan Co., Ltd.) to which was further added 25 parts of a curing agent (NP-400, produced by Sankyo Chemical Industries, Co., Ltd.), mixed thoroughly and poured onto a red adhesive tape. After five hours at room temperature, there was obtained a yellow opaque sheet. This sheet was allowed to stand in a constant temperature chamber at 30° C. Three months later, the entire red tape on the back surface of the sheet was visible from the front surfaces.

While the invention has been described in detail and with reference to specific embodiments thereof, it will be apparent to one skilled in the art that various changes and modifications can be made therein without departing from the spirit and scope thereof.

What is claimed is:

1. In a resin molded controlled-release product which comprises a volatile or elutable active agent dispersed in a substantially transparent and inert resin molded material, the improvement which comprises a colored material located inside or on the back surface of the molded product which is not visible through the product at the initial concentrations of the active agent, but is visible through the resin product at concentrations of the active agent at which the activity of the product is substantially extinct.

2. The resin molded product of claim 1 which is characterized by being in the form of a sheet or film and including a colored layer and/or a message on its back surface.

3. The resin molded product of claim 1 which is characterized by being in the form of a sheet or film, including a colored layer and/or a message on its back surface and further including an adhesive layer on the under surface of said colored layer and/or said message.

4. The resin molded product of claim 1 which is characterized by being a plurality of sheets or films adhered to one another and including a colored layer and/or a message between the intermediate sheets or films or on the back surface of the undermost layer sheet or film.

5. The resin molded product of claim 1 which is characterized by being in a sphercial or polyhedral form and including a colored layer and/or a message therein.

6. A method for indicating extinction of activity in a resin molded controlled-released product which comprises rendering a normally transparent resin opaque by incorporation of an active agent therein and providing within or on the surface of said molded product, a colored material such that upon evaporation or elution of the active ingredient from said product to extinction, said resin becomes transparent and said colored material is visible through the resin product.

* * * * *